United States Patent [19]
Smith et al.

[11] Patent Number: 5,708,154
[45] Date of Patent: Jan. 13, 1998

[54] RNA-DNA HYBRID MOLECULES OF NUCLEIC ACID

[75] Inventors: Steven S. Smith, Los Angeles; Bruce E. Kaplan, Claremont, both of Calif.

[73] Assignee: City of Hope, Duarte, Calif.

[21] Appl. No.: 745,922

[22] Filed: Aug. 16, 1991

Related U.S. Application Data

[63] Continuation-in-part of Ser. No. 598,665, filed as PCT/US90/00884, Feb. 23, 1990, abandoned, and a continuation-in-part of Ser. No. 317,670, Mar. 1, 1989, abandoned, and a continuation-in-part of Ser. No. 314,935, Feb. 24, 1989, abandoned.

[51] Int. Cl.$^6$ .............................. C07H 21/00; C12Q 1/68
[52] U.S. Cl. ..................... 536/23.1; 435/6; 435/7.5; 435/91.1; 435/91.51; 536/22.1; 536/25.3; 536/25.32; 536/25.34
[58] Field of Search .................... 536/27, 28, 29, 536/23.1, 25.3, 25.32, 25.34, 25.1; 435/6, 28, 7.5, 91.1, 91.51

[56] References Cited

U.S. PATENT DOCUMENTS

| 4,762,779 | 8/1988 | Snitman | 536/25.32 |
|---|---|---|---|
| 4,794,073 | 12/1988 | Dattagupta et al. | 435/6 |
| 4,859,768 | 8/1989 | Suhaddnik et al. | 536/25.1 |
| 5,011,769 | 4/1991 | Duck et al. | 536/23.1 |
| 5,047,519 | 9/1991 | Hobbs, Jr. et al. | 536/23 |
| 5,215,899 | 6/1993 | Dattagupta et al. | 435/6 |

OTHER PUBLICATIONS

Alberts et al., The Molecular Biology of the Cell, pp. 188–190, 1983.

*Primary Examiner*—James O. Wilson
*Attorney, Agent, or Firm*—Rothwell, Figg, Ernst & Kurz

[57] ABSTRACT

Molecules having an RNA block linked to a shorter DNA block is described. The RNA and DNA blocks are complementary to accommodate formation of fold-back molecules having a 3' hydroxyl on the DNA block and an overhanging RNA strand at the end of a short DNA-RNA hybrid.

20 Claims, 2 Drawing Sheets

X: Inhibitory Substitution, e.g. 1,4 Anhydro-D-Ribitol.
Y: Inhibitory Substitution, e.g. Cordycepin (3'deoxyAdenosine).

RNA-DNA HYBRID MOLECULES OF NUCLEIC ACID

RELATED APPLICATIONS

This application is a continuation-in-part of each of Smith and Kaplan application Ser. No. 07/598,665 filed as PCT/US90/00884, Feb. 23, 1990, now abandoned, U.S. Pat. No. 90/00884, filed Feb. 23, 1990, now abandoned, Ser. No. 07/317,670 filed Mar. 1, 1989, now abandoned and Ser. No. 07/314,935 filed Feb. 24, 1989, now abandoned.

FIELD OF INVENTION

The copending related applications relate to heterologous block oligomers (HBO's). This invention relates to new classes of HBO's identified as modular nanostructure (MNS's) and to the use of MNS's in the detection and inhibition of retroviral reverse transcriptase. The invention also relates to radio-label free reverse transcriptase assays involving MNS's, to the use of such assays to screen antiviral drugs and to novel reverse transcriptase inhibitors.

BACKGROUND OF THE INVENTION

The related parent applications describe inventions which utilize the capacity of nucleic acids for self assembly to construct a series of unimolecular DNA foldbacks or HBO's that are good enzyme substrates. In these molecules a long block of DNA is linked through a tether to a complementary short block of DNA. The tether may consist of dT residues, biotin residues, dodecyl phosphate residues, aminopropyl phosphate residues, or trivalent residues which are similar to the above but will allow for side-chain modification. These modifications may include chemiluminescent, fluorescent, or biotin moieties. The tether promotes intramolecular hybridization of the two regions of complementary DNA to form foldbacks having a free 3' hydroxyl on the short DNA strand and an overhanging DNA strand at the end of a short DNA-DNA hybrid. Appropriate HBO's have been shown to be substrates for restriction enzymes, human DNA methyl transferase and DNA polymerase I from E. coli.

Relevant to this invention is the discovery that DNA polymerase I is effective in extending each of the tethered foldbacks to a discrete length corresponding to full extension of the short block in the foldback using the 5' overhang as a template. Variation in the type of tether used permits chromatographic discrimination between otherwise isomeric forms of the molecules.

SUMMARY OF THE INVENTION

Somogyi, *Journal of Virological Methods*, 27: 269–276 (1990) describes a solid phase reverse transcriptase microassay. Biotin is suggested as a replacement for tritium in the extant procedures. The invention provides modular nanostructures for use in the detection and inhibition of retroviral reverse transcriptase. For such purposes a relatively short block of DNA is linked to a longer block of RNA through a short tether of variable chemical composition. The tethered blocks are complementary to accommodate the formation of unimolecular foldbacks having a 3' hydroxyl on the DNA strand and an overhanging RNA strand at the end of a short DNA-RNA hybrid.

For reverse transcriptase detection, the tether will include labelled, preferably fluorescent moieties. Incubation of the foldback molecule with biotinylated nucleotide triphosphate precursors in the presence of reverse transcriptase yields a fluorescent product that can be concentrated by affinity binding to matrix bound avidin and detected by fluorescence.

For reverse transcriptase inhibition in living cells, the tether includes hydrophobic moieties to permit transport in liposomes and the penetration of cell membranes. The nanostructure for reverse transcriptase detection or inhibition may include appropriate substitutions. For example, to block enzyme activity, a stable abasic site analog may be included in the RNA strand or a cordycepin moiety may be present at the 3' end of the DNA strand.

DETAILED DESCRIPTION OF THE INVENTION

The expansion of the AIDS epidemic worldwide to between 10 and 30 million HIV positive individuals creates an urgent need for reliable and cost-effective HIV testing and for the screening of potential anti-viral drugs. The need is the greater due to other retroviral diseases such as hairy cell leukemia.

In one important embodiment, this invention provides a simply, highly sensitive, assay for HIV and other retroviral transcriptases which does not employ a radiolabel. This embodiment of the invention facilitates the direct screening of antiviral drugs by the rapid laboratory determination of viral titer in drug treated samples such as cell lines.

Another aspect of the invention permits evaluation of substrate specificity of HIV and other reverse transcriptases and so facilitates the design of deliverable inhibitors.

Figure 1:
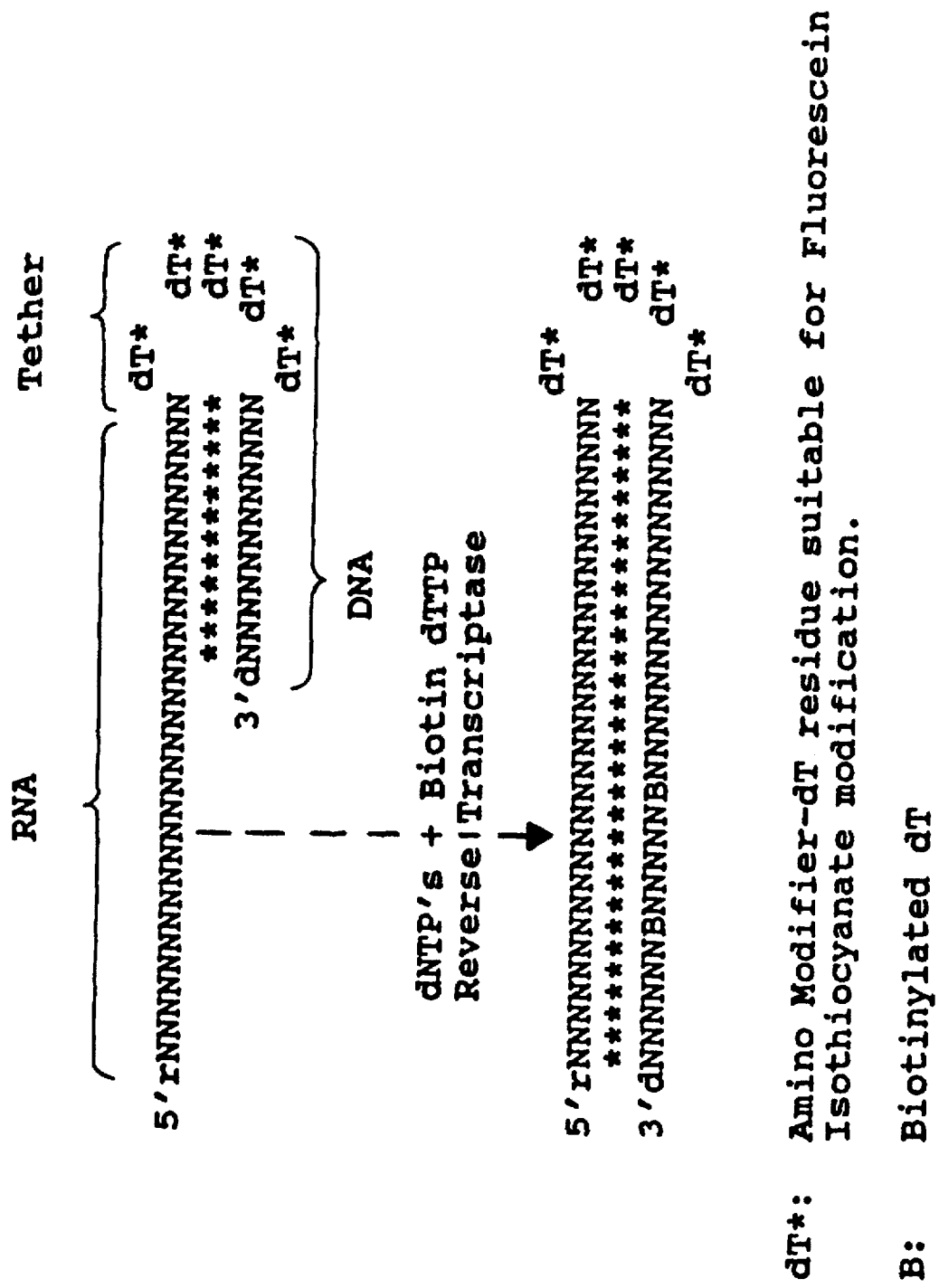
FIG. 1 illustrates the experimental design for the production of labelled biotinylated MNS's and the use thereof to detect reverse transcriptase activity.

FIG. 1 illustrates generally the synthesis of a RNA module 30 nucleotides in length from commercially available ribonucleotide precursors. As shown, five functionally modified "dT" moieties are then added to provide a fluorescent label in a tether module. The linked DNA module consists of 10 deoxynucleotides to provide Watson-Crick homology with the 3' end of the 30 mer and thus form the folded substrate molecule (MNS) shown in FIG. 1.

Incubation of this substrate molecule with active reverse transcriptase in the presence of biotinylated deoxynucleotide precursors yields the biotinylated product shown in FIG. 1.

The extent of recovery of the fluorescent product with an avidin based matrix, e.g., in a streptavidin agarose minicolumn, is a function of the activity of reverse transcriptase.

The fluorescent product is quantitated by fluorimetry.

Advantages of this procedure for detecting and quantitating reverse transcriptase are (1) radioactive compounds are not required; (2) sensitivity can be increased by increasing sample size and concentrating the product; and (3) the sequence of the substrate MNS's and its composition—i.e., RNA-DNA; RNA—RNA, can be chosen to optimize the observed activity or increase its specificity for a given species of reverse transcriptase.

A practical application of this aspect of the invention is an assay to detect or quantify reverse transcriptase in physiological samples. The assay entails procurement of a sample from a patient suspected of viral infection, e.g., a patient who may be HIV positive, incubating the sample in the presence of a biotinylated triphosphate with a MNS having a fluorescent tether, recovering the biotinylated product, if any, on an avidin matrix, and quantifying the biotinylated product if present.

The invention includes kits comprising an appropriate fluorescent labelled MNS, and biotinylated dioxynucleotide triphosphate precursor.

EXAMPLE I

Synthesis and Use of a Simple Reverse Transcriptase Substrate

The sequence of each of the three modules in the HBO can be chosen by the investigator. Sequences identical to those of the HIV, and HTLV-I initiation site may be especially useful. In order to provide clarity in this example a simple sequence is used to illustrate the method.

HBO Synthesis

Synthesis of the HBO begins with the 3' matrix-bound phosphoramidite precursor of thymidine (dT). Programmed DNA synthesis is continued using standard methods in an ABI DNA synthesizer until 12 residues of dT have been added. This constitutes the complementary DNA module. The loop module is synthesized beginning with the addition of two dC residues, after which the system reaches a preprogrammed stop. At this point the investigator manually carries out one cycle of DNA synthesis in which a trifunctional dT residue carrying a masked primary amine is added to the growing chain. Two additional dC residues are added to the growing chain to complete the loop module. The RNA module in the HBO is begun by the addition of 30 adenasine (A) residues using protected riboprecursors and standard RNA synthesis methods. Once the HBO is completed, it is cleaved from the matrix and the masked amino group on the trifunctional dT residue in the loop module is reacted with fluorescein isothiocyanate (FITC).

Based on previous work with partially complementary molecules of this type, the HBO will self-associate to form the modular nanostructure depicted below.

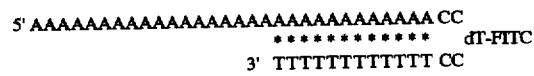

Based on experience with DNA polymerases, this nanostructure is expected to be a self-priming substrate for reverse transcriptase.

Reverse Transcriptase Assay

A standard reaction mixture containing: 50 mM Tris-HCl (pH 8.3), 40 mM KCl, 6 mM MgCl$_2$, 1 mM Dithiothreitol, 0.1 mg/ml RNAse free bovine serum albumin and 0.1 mM HBO substrate is then incubated with a reverse transcriptase preparation in 50 µl total volume for 10 minutes at 37° C. in the presence of 0.5 mM Biotinylated dTTP.

HBO's that have been extended by reverse transcriptase will now contain at least 1 biotinylated dT residue, and will therefore be retained by commercially available streptavidin-Agarose. The reverse transcriptase product will be isolated by passage of the complete reaction mixture through a 50 µl column of commercially available streptavidin agarose. After washing with 1 ml of Tris-HCl (pH 8.3), 400 mM KCl, the amount of fluorescein-containing substrate retained by the agarose can be quantified by fluorimetry on the suspended agarose slurry. Alternatively the fluorescein-containing substrate can be eluted from the agarose with a solution containing a strong denaturant, like 6M guanidine HCl at pH 1.5, and fluorometric quantification of the fluroescein-containing substrate can be carried out in a neutralized solution.

Figure 2:
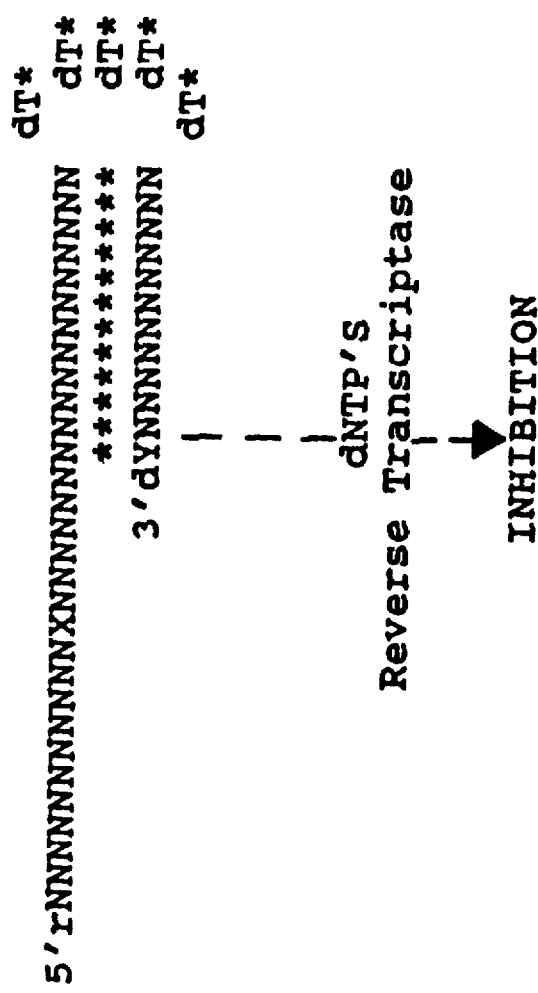
FIG. 2 illustrates the experimental design for development of a family of reverse transcriptase inhibitors based, in part, on substitution in the modular nanostructure.

FIG. 2 illustrates procedures for preparing one or more reverse transcriptase inhibitors based on substitutions in the nanostructure. A MNS similar to that shown in FIG. 1 is utilized with the exception that the amino modifier dT used in the tether is a hydrophilic moiety, i.e., dodecylphosphate to facilitate liposome transport, and an enzyme inhibitory substitution, e.g., 1,4-anhydro-D-ribitol is present in the RNA template of the nanostructure. An enzyme inhibitory moiety, e.g., cordycepin (3'deoxyadenosine) may alternatively or additionally be included at the 3' end of the DNA strand.

Inhibition of HIV reverse transcriptase is accomplished by incorporation of the MNS's into liposomes for transport to and penetration of cell membranes.

EXAMPLE II

Synthesis of a Simple Reverse Transcriptase Inhibitor

As with the HBO described in Example I, a simple sequence is used to illustrate the preparation of an inhibitory substrate.

HBO Synthesis

Synthesis of the HBO begins with the 3' matrix-bound phosphoramidite precursor of thymidine (dT). Programmed DNA synthesis is continued using standard methods in an ABI DNA synthesizer until 12 residues of dT have been added. This constitutes the complementary DNA module. The loop module is then synthesized by adding 5 dC residues to the growing chain using standard methods. The RNA module in the HBO is begun by the addition of 15 adenine (A) residues using protected riboprecursors and standard RNA synthesis methods, after which the system reaches a preprogrammed stop. The investigator then performs one cycle of manual DNA synthesis to introduce a 1,4-anhydro-D-ribitol (x) phosphoramidite into the growing RNA module. The RNA module is then completed by the automated addition of 14 additional adenine (A) residues.

Based on our previous work with partially complementary molecules of this type, the HBO will self-associate to form the modular nanostructure depicted below.

```
5' AAAAAAAAAAAAAAAxAAAAAAAAAAAAAA CC
                  ************     C
               3' TTTTTTTTTTTT CC
```

As noted above, the nanostructure is expected to be a self-priming substrate for reverse transcriptase. Analogous DNA substrates inhibit DNA polymerases because the abasic site analog does not provide a mechanism for base-pair formation with an incoming nucleoside triphosphate precursor. Thus the nanostructure depicted above is expected to permit initiation but block elongation by reverse transcriptase after the addition of three nucleotides to the DNA module. Thus its net effect is to inhibit the enzyme.

We claim:

1. A modular nanostructure comprising (i) a thirty base RNA sequence;

(ii) a ten base DNA sequence said DNA sequence being hybridized to the 10 bases adjacent the 3' terminus of said RNA sequence to provide an unhybridized 20 base sequence at the 5' terminus of said RNA sequence, and (iii) a five dT moiety tether connecting the 3' terminal nucleotide of said RNA sequence to the 5' terminal nucleotide of said DNA sequence.

2. A modular nanostructure as defined by claim 1 in which said tether has a fluorescent label.

3. A modular nanostructure as defined by claim 1 in which the dT moiety is hydrophilic.

4. A modular nanostructure as defined by claim 1 in which said RNA sequence includes an enzyme inhibiting moiety.

5. A modular nanostructure as defined by claim 4 in which said enzyme inhibitor is 1,4 anhydro-D-ribitol or 3' deoxyadenosine.

6. A molecule having the schematic formula:

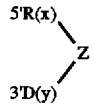

in which R is an RNA sequence of x nucleotides, D is a DNA sequence of y nucleotides, Z is an organic moiety linking the 3' terminal nucleotide of R with the 5' terminal nucleotide of D, and the value of x is more than the value of y a 3' terminal portion of R adjacent Z being complementary to a 5' terminal portion of D adjacent Z wherein said 3' and 5' terminal portions of R and D hybridize to provide an RNA-DNA hybrid sequence, and an unhybridized 5' terminal portion of R.

7. A molecule as defined by claim 6 in which Z comprises dT residues.

8. A molecule as defined by claim 6 in which Z is labelled.

9. A molecule as defined by claim 6 in which R or D are substituted by an enzyme inhibiting moiety.

10. A molecule as defined by claim 6 in which R is substituted by 1,4 anhydro-D-ribitol or 3' deoxyadenosine.

11. A modular nanostructure consisting of
    (i) a thirty base RNA sequence;
    (ii) a ten base DNA sequence said DNA sequence being hybridized to the 10 bases adjacent the 3' terminus of said RNA sequence to provide an unhybridized 20 base sequence at the 5' terminus of said RNA sequence, and
    (iii) a five dT moiety tether connecting the 3' terminal nucleotide of said RNA sequence to the 5' terminal nucleotide of said DNA sequence.

12. A modular nanostructure as defined by claim 1 in which said tether has a fluorescein isothiocyanate label.

13. A modular nanostructure as defined by claim 1 in which said RNA sequence has a single substituent, said single substituent being 1,4 anhydro-D-ribitol or 3' deoxyadenosine.

14. A molecule having the schematic formula:

in which R is an RNA sequence of x nucleotides, D is a DNA sequence of y nucleotides, Z is a sequence of dT residues and the value of X is greater than the value of y and in which a 3' terminal portion of R adjacent Z is complementary to a 5' terminal portion of D adjacent Z;

wherein said 3' and 5' terminal portions of R and D are hybridized to provide an RNA-DNA hybrid sequence, and an unhybridized 5' terminal portion of R.

15. A molecule as defined by claim 6 in which Z consists of dT residues.

16. A molecule as defined by claim 6 in which Z consists of dT residues and in which Z has a fluorescein isothiocyanate label.

17. A molecule as defined by claim 6 in which either R or D has a single substituent and where said single substituent is 1,4 anhydro-D-ribitol or 3' deoxyadenosine.

18. A molecule as defined by claim 6 in which Z consists of five dT residues, R is a thirty base RNA sequence, D is a ten base DNA sequence, wherein D is hybridized to the ten bases adjacent the 3' terminus of R.

19. A molecule as defined by claim 6 in which R or D has a single enzyme inhibiting moiety attached thereto and in which said enzyme inhibiting moiety is 1,4 anhydro-D-ribitol or 3' deoxyadenosine.

20. A molecule having the formula:

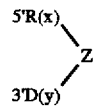

in which R is an RNA sequence of x nucleotides, D is a DNA sequence initially of y nucleotides, Z is an organic moiety linking the 3' terminal nucleotide of R with the 5' terminal nucleotide of D, and the value of x is more than the value of y;

a 3' terminal portion of R adjacent Z being complementary to a 5' terminal portion of D adjacent Z wherein said 3' and 5' terminal portions of R and D hybridize to provide an RNA-DNA hybrid sequence, and an unhybridized 5' terminal portion of R; and in which the 3' terminal position of D has been extended by reverse transcriptase in the presence of a biotinylated deoxynucleotide precursor so that D is a DNA sequence of x nucleotides and in which the D sequence includes biotinylated nucleotides in the region corresponding to the previously unhybridized portion of the R sequence.

* * * * *

UNITED STATES PATENT AND TRADEMARK OFFICE
CERTIFICATE OF CORRECTION

PATENT NO. : 5,708,154
DATED : January 13, 1998
INVENTOR(S) : Steven S. Smith et al.

It is certified that error appears in the above-indentified patent and that said Letters Patent is hereby corrected as shown below:

<u>In the Claims:</u> Col. 5, line 42 (claim 12), "claim 1" should be -- claim 11 --; Col. 5, line 44 (claim 13), "claim 1" should be -- claim 11 --.

Signed and Sealed this

Twenty-first Day of July, 1998

Attest:

BRUCE LEHMAN

Attesting Officer

Commissioner of Patents and Trademarks